(12) United States Patent
Jenkins et al.

(10) Patent No.: US 6,642,513 B1
(45) Date of Patent: Nov. 4, 2003

(54) MATERIALS AND APPARATUS FOR THE DETECTION OF CONTRABAND

(75) Inventors: Anthony Jenkins, North Reading, MA (US); William J. McGann, Raynham, MA (US); Joseph Napoli, Wyndham, NH (US); Kevin Perry, Dracut, MA (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/411,455

(22) Filed: Oct. 1, 1999

Related U.S. Application Data

(60) Provisional application No. 60/103,168, filed on Oct. 6, 1998.

(51) Int. Cl.[7] .......................... H01J 49/00; G01N 00/00; G01N 7/00; G01N 9/00
(52) U.S. Cl. .......................... 250/288; 250/281; 23/864; 23/863.12; 23/23.2
(58) Field of Search ................. 250/288, 281; 73/864, 864.7, 863.12, 23.2

(56) References Cited

U.S. PATENT DOCUMENTS

| | | | |
|---|---|---|---|
| 3,596,440 A | * | 8/1971 | Nutter .......................... 55/320 |
| 3,968,297 A | | 7/1976 | Sauer |
| 4,045,997 A | * | 9/1977 | Showalter et al. .......... 340/632 |
| 4,731,283 A | | 3/1988 | Sakane et al. |
| 4,772,794 A | * | 9/1988 | Jenkins .......................... 250/382 |
| 4,781,972 A | | 11/1988 | Sakane et al. |
| 4,788,226 A | * | 11/1988 | Curry ..................... 210/500.38 |
| 4,964,309 A | * | 10/1990 | Jenkins ......................... 340/632 |
| 4,997,067 A | | 3/1991 | Watts |
| 5,232,770 A | * | 8/1993 | Joseph .......................... 156/167 |
| 5,342,434 A | * | 8/1994 | Wu ................................. 96/13 |
| 5,405,781 A | * | 4/1995 | Davies et al. ................. 250/282 |
| 5,491,337 A | | 2/1996 | Jenkins et al. |
| 5,741,984 A | | 4/1998 | Danylewych-May et al. |
| 5,760,314 A | * | 6/1998 | Bromberg et al. ........ 73/863.21 |
| 5,859,362 A | * | 1/1999 | Neudorfl et al. .............. 73/23.2 |
| 5,859,375 A | * | 1/1999 | Danylewych-May et al. ........................ 73/864.71 |
| 5,915,268 A | * | 6/1999 | Linker et al. .................. 422/93 |
| 5,922,104 A | * | 7/1999 | Park et al. ...................... 95/51 |
| 6,169,045 B1 | * | 1/2001 | Pike et al. .................... 442/352 |
| 6,261,979 B1 | * | 7/2001 | Tanaka et al. ............. 210/493.5 |
| 6,375,886 B1 | * | 4/2002 | Angadjivand et al. ...... 264/115 |

FOREIGN PATENT DOCUMENTS

EP        0 247 243        12/1987

OTHER PUBLICATIONS

Extraction, transportation and processing of explosives vapor in detector systems, A. Jenkins et al., May 1992, Proceedings of the first international symposium on explosive detection technology, pp. 532–551.*

* cited by examiner

Primary Examiner—John R. Lee
Assistant Examiner—K Fernandez
(74) Attorney, Agent, or Firm—Anthony J. Casella; Gerald E. Hespos

(57) ABSTRACT

Sample traps or wipes are provided for a detection system for detecting contraband materials. The sample trap is formed from an open weave glass fabric coated with a thin layer of Teflon and roughened to cut through the surface of Teflon and to break some of the glass fibers. Alternatively, the sample trap is non-woven felt fabric made of high temperature polyamide fiber. The sample traps are used in a detector, such as an ion trap mobility spectrometer. The detector includes a desorber which feeds dry air from a manifold above and below the sample trap through a series of holes along the mouth of the desorber. The dry air passes through the trap and purges out unwanted atmospheric constituents that could otherwise affect the performance of the detector. The purged air passes to the outside atmosphere, thus creating a dry curtain at the entry to the desorber.

3 Claims, 6 Drawing Sheets

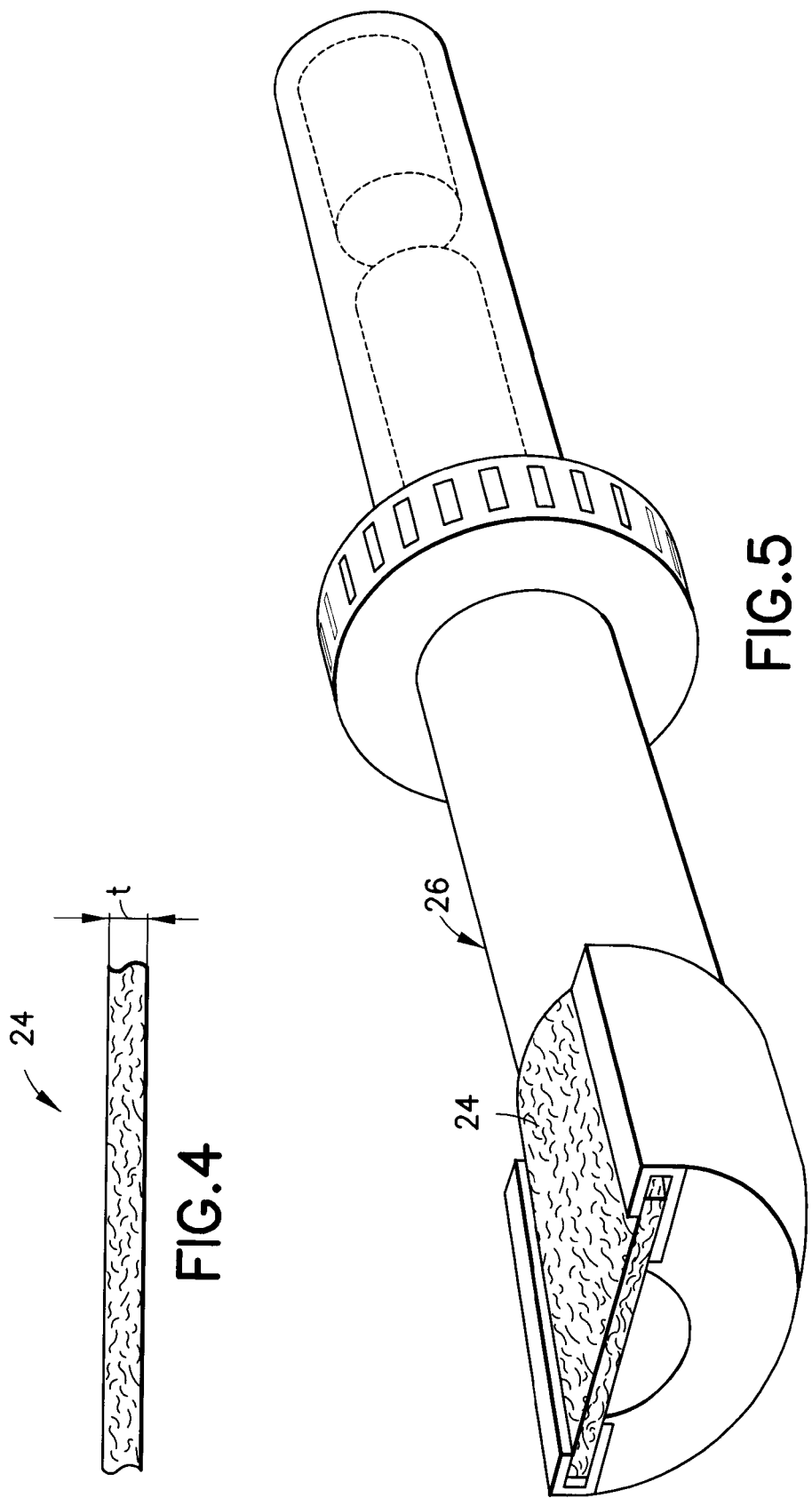

MATERIALS AND APPARATUS FOR THE DETECTION OF CONTRABAND

This application claims the benefit of U.S. Provisional Patent Appl. No. 60/103,168 filed Oct. 6, 1998.

BACKGROUND OF THE INVENTION

1. Field of the Invention

The subject invention is directed to materials that can be used to collect traces of contraband. The subject invention also is directed to an apparatus for detecting trace particles and condensed vapors of contraband.

2. Description of the Prior Art

Detection systems exist for detecting particulate and condensed phase traces of materials, such as narcotics and explosives. Such systems are marketed by Ion Track Instruments, Inc., which is the assignee of the subject invention. One system of Ion Track Instruments, Inc. is shown in U.S. Pat. No. 5,491,337. Other systems for these general purposes are marketed by Barringer Technologies Inc. under the name Ion Scan Detection Systems and by Intelligent Detection Systems of Canada, under the name Sirius. These prior are systems are deployed, for example, at airports to detect and prevent the introduction of explosives and to detect and deter the traffic in narcotics.

The prior art detection systems rely upon the fact that trace amounts of contraband will be transferred to the body of a person who had handled the contraband and subsequently will be transferred from the body to any article the person may be carrying (e.g., purse, suitcase, backpack, etc.). Trace amounts of contraband may be collected for analysis by wiping a small sheet-like wipe or trap across the purse, suitcase, backpack or other article of the suspect. The prior art wipe or trap then is inserted into a prior art detection apparatus which tests for the presence of certain contraband particles or vapors.

Sample wipes or traps used in such prior art detection apparatus typically have been made of paper, cotton cloth or porous PTFE (Teflon). Each of these prior art sampling media have their own shortcomings. For example, pure Teflon material has a very low coefficient of friction, and therefore does not efficiently remove small particles from rough surfaces. Paper and cotton wipes or traps, on the other hand, may pick up particles more efficiently. However, paper and cotton also pick up water. As a result, they delay the evaporation process of the target materials and inhibit the response. Therefore, prior art paper and cotton wipes or traps are not well suited for use on surfaces that may be wet. Although these prior art sample wipes are fairly efficient for detecting particulates, they are significantly less efficient for detecting vapor. In particular, Teflon is not the best vapor trap, and paper has many active sites which do not release the trapped vapor after the sample wipe has been placed in a detection apparatus.

The prior art detection systems typically rely upon a sample being collected on a sampling medium, such as the above-described sample wipes or traps. These samples may be transferred physically into the prior art detection apparatus as identified above. Alternatively, the sampling medium itself may be heated. The heat is intended to cause at least portions of the sample to be evaporated and then drawn into the detection system on an air stream. This latter prior art method generally is preferred because it allows the detection of condensed vapors which may have been collected, as well as any particulate material.

An existing system sold by Ion Track Instruments, Inc. is illustrated schematically in FIG. 1. This prior art system of FIG. 1 is similar to the system described in greater detail in the above-referenced U.S. Pat. No. 5,491,337. The prior art system of FIG. 1 analyzes samples that are collected on sample wipes consisting of a clean porous filtered paper. These wipes are dropped into a thermal desorber 12 in FIG. 1. Desorbed material is carried into the detector by the action of a sampling pump 14. The sample air is drawn into the detector 16 over a dimethyl silicone membrane 18. Some contraband or other materials of interest diffuse through the membrane 18 and into the detector 16, which may be an ion mobility spectrometer or an ion trap mobility spectrometer. The dimethyl silicone membrane 18 eliminates all dust, dirt and most atmospheric materials, including water, all of which may cause problems in the detector 16. Unfortunately, the membrane 18 is only a few percent efficient at transferring the materials of interest, and this efficiency can limit the ultimate sensitivity of the apparatus 10.

In view of the above, it is an object of the subject invention to provide a filter material for sampling vapor and particulates which enables air flow through the material for vacuum sampling.

It is another option of the subject invention to provide an efficient sample pick-up that is suitable for use on rough surfaces and that will perform well on wet surfaces.

It is another object of the subject invention to provide sample pick-up material that is low in cost and/or that is resuable.

A further object of the subject invention is to provide a detection system that retains the advantages of the prior art systems, while improving the efficiently of the transfer of materials of interest into the detector.

SUMMARY OF THE INVENTION

The subject invention is directed to an improved sampling medium for a detection system and to a detection system with improved performance.

The sampling medium of the subject invention may be an open weave glass fabric which is coated with a thin layer of Teflon. The coating is carried out in such a manner to leave spaces open between the respective fibers of the fiberglass web. Similar materials are used for specialty conveyor belts, and such conveyor belts are marketed by Greenbelt Industries. Small patches of this open weave glass fabric coated with Teflon picks up particulate matter from wet and dry surfaces simply by wiping the small patch of material across the surface. However, the prior art open weave glass fabric coated with Teflon, as used on conveyor belts, is not efficient for picking up samples of material of interest from rough or pitted surfaces. It has been found that the efficiency of pick-up can be improved significantly by roughening the surface with an abrasive to cut through the surface of the Teflon coating at a plurality of spaced-apart locations and to break some of the glass fibers free. This produces a three-dimensional surface, with the broken fibers extending angularly from the plane of the material substantially in the manner of a brush. The fibers act as a scrubbing material and pick-up small particles into the matrix. The Teflon has been found to hold the remaining weave together and to enhance durability of the sample trap.

The sample traps can be manufactured by starting with prior art open weave glass fabric coated with Teflon and intended for the above-referenced specialty conveyor belts. The fabric then may be subjected to an abrasive action to cut through the surface of the Teflon and to break some of the glass fiber free into the above-referenced brush-like configuration. The elongate sheet of material then is subjected to punching or cutting to produce small circular or rectangular traps.

An alternate trap or wipe material is a non-woven felt fabric made of high temperature polyamide fiber. This material is more abrasive than Teflon, and therefore for many applications may not require the abrasive treatment of the above-referenced glass woven fabric that had been coated with Teflon. Additionally, the non-woven felt fabric made of high temperature polyamide fiber exhibits superior high temperature performance. The preferred embodiment is a thin sheet with a thickness of less than 3 mm. Wipes of this type have been found to allow a high flow of air when a small vacuum is applied to one side. The material retains both large and small particles, and also traps vapors from low volatility contraband, such as cocaine vapor or plastic explosives vapors. The non-woven felt fabric made of high temperature polyamide fiber also has a low thermal inertia, which allows the trap to be heated rapidly to temperatures exceeding 200° C., where most contraband of interest evaporates rapidly.

A detection system that may be used with the sample wipes described above employs a desorber to purge the sample wipe of unwanted atmospheric constituents and volatile contaminants. These unwanted atmospheric constituents, such as water vapor and oxides of nitrogen upset the detection process. This purging is achieved in the desorber by feeding dry air from a manifold above and below the sample wipe or trap through a series of small holes along the mouth of the desorber. Alternatively, the dry air may be directed through a narrow slot or through other means for creating an air curtain. The dry air passes through the wipe and purges out the ambient air. The purged air then passes to the outside atmosphere, thus creating a dry air curtain at the entry to the desorber. A portion of the dry air fed through the manifold system presses down the desorber. As the trap or wipe is introduced into the desorber, it quickly obtains the temperature of the desorber. The materials of interest evaporate and are carried on the air stream of dry air into the detector. The detector preferably is an ion mobility spectrometer or an ion trap mobility spectrometer as described above with reference to FIG. 1 and as described in significantly greater detail in U.S. Pat. No. 5,491,337.

In another embodiment, the trap or wipe is operated by an automated actuator. The actuator pushes the trap in and out of the desorber, but does not pull it completely out. In the outer position, a high flow of air is drawn through the trap by the action of a vacuum pump. Any material which is drawn into the trap, is captured, and subsequently introduced into the desorber by actuating the trap into the desorber. The material captured by the trap is evaporated in the desorber as described above, and is passed into the detector.

The above-described trap system can be incorporated into a walk-through configuration. In this latter embodiment, air is allowed to flow over the subject's body either horizontally or vertically. For example, the trap can be disposed in a portal through which the subject may move. Preferably, the trap is disposed at a location in the portal vertically above the subject. The air then is caused to flow through the trap mounted near the test subject by the action of a suction pump. All vapors and particles entrained in the air sample are trapped in the trap and subsequently are detected.

The trap material in this latter embodiment traps samples only from an air stream, and is not used to wipe surfaces. This gives an opportunity for using trap materials which may otherwise be too abrasive. An example of a suitable material is a stainless steel filter material, which provides good trapping efficiency for vapors, as well as good trapping of particles.

BRIEF DESCRIPTION OF THE DRAWINGS

FIG. 4 is a side elevational view of a second embodiment of a trap.

FIG. 5 is a perspective view of a vacuum sampler employing the trap of FIG. 4.

DETAILED DESCRIPTION OF THE PREFERRED EMBODIMENTS

Figure 3:
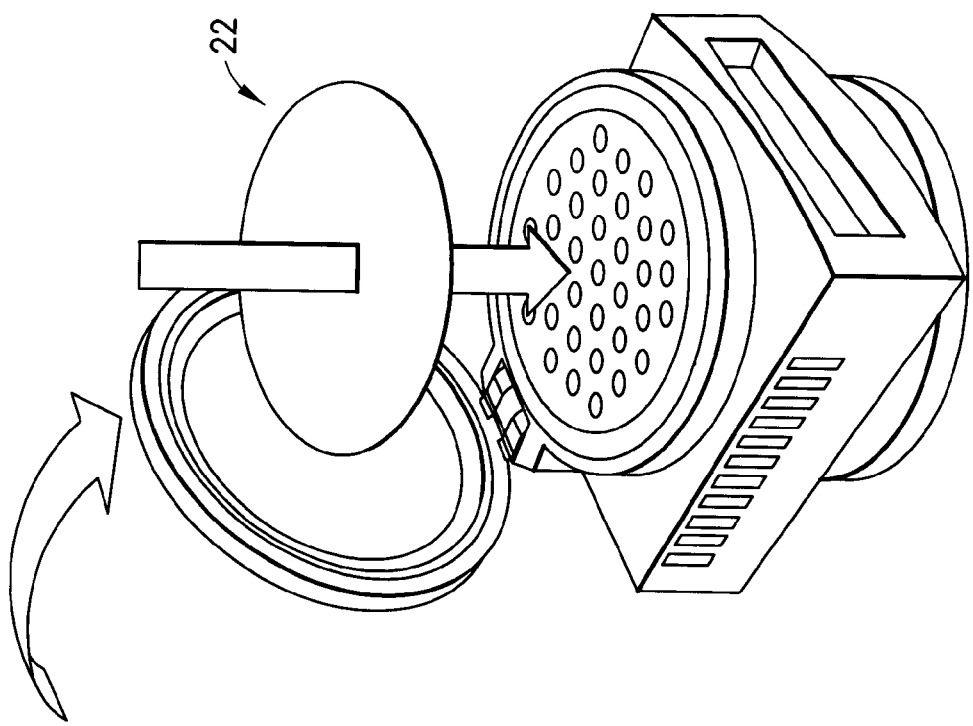
FIG. 3 is a perspective view showing the trap being placed in a detection apparatus.
Figure 2:
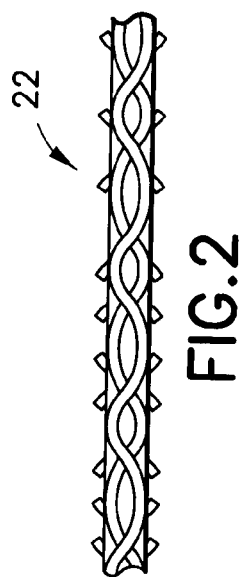
FIG. 2 is a side elevational view of a trap in accordance with a first embodiment of the subject invention.

A sample trap in accordance with a first embodiment of the subject invention is identified generally by the numeral 22 in FIGS. 2 and 3. The sample trap 22 is formed from an open weave glass fabric coated with a thin layer of PTFE (Teflon). The weaving and coating is carried out such that open spaces are defined between the elements of the fiberglass web. The initial product may be a conveyor belt, such as the specialty conveyor belts marketed by Greenbelt Industries. However, the open weave glass fabric coated with Teflon and used for specialty conveyor belts is roughened with an abrasive material to cut through the surface of the Teflon at selected locations on the woven fiberglass fabrics and to break some of the glass fibers free. Thus, as shown schematically in FIG. 2, short sections of glass fibers will be directed away from the plane of the fabric in substantially the manner of a brush. These broken fibers act as a scrubbing material and pick up small particles into the matrix for subsequent analysis in a detection apparatus as explained further herein. The roughened woven glass fabric then is subjected to a punching or cutting operation to produce small sample traps that are appropriately configured and dimensioned for the particular detection apparatus. More specifically, as shown in FIG. 3, the roughened coated glass fabric has been punched into the circular sample trap. In other embodiments, the fabric may be cut into rectangular squares.

An alternate embodiment of the subject sample trap is identified generally by the numeral 24, and is illustrated schematically in FIG. 4. This alternate trap is a non-woven felt fabric made of a high temperature polyamide fiber. The trap 24 has a thickness "t" as shown in FIG. 4 of less than 3 mm, and preferably in the range of approximately 1–2 mm. This material allows a high flow of air when a small vacuum is applied to one side of the trap 24. The material is more abrasive then a Teflon fabric, and therefore retains both large and small particles and also traps vapors from low volatility contraband, such as cocaine vapor and plastic explosives vapors. The non-woven high temperature polyamide fiber of the trap 24 has a superior high temperature performance and a low thermal inertia. The low thermal inertia allows the trap 24 to be heated rapidly to temperatures exceeding 200° C., which is a temperature where most contrabands of interest evaporate rapidly. The sample trap 24 may be used in an apparatus substantially in the manner shown in FIG. 3 above. Alternatively, the trap 24 may be cut into a rectangular shape and may be used in a hand-held vacuum sampler 26, as shown in FIG. 5.

Figure 1:
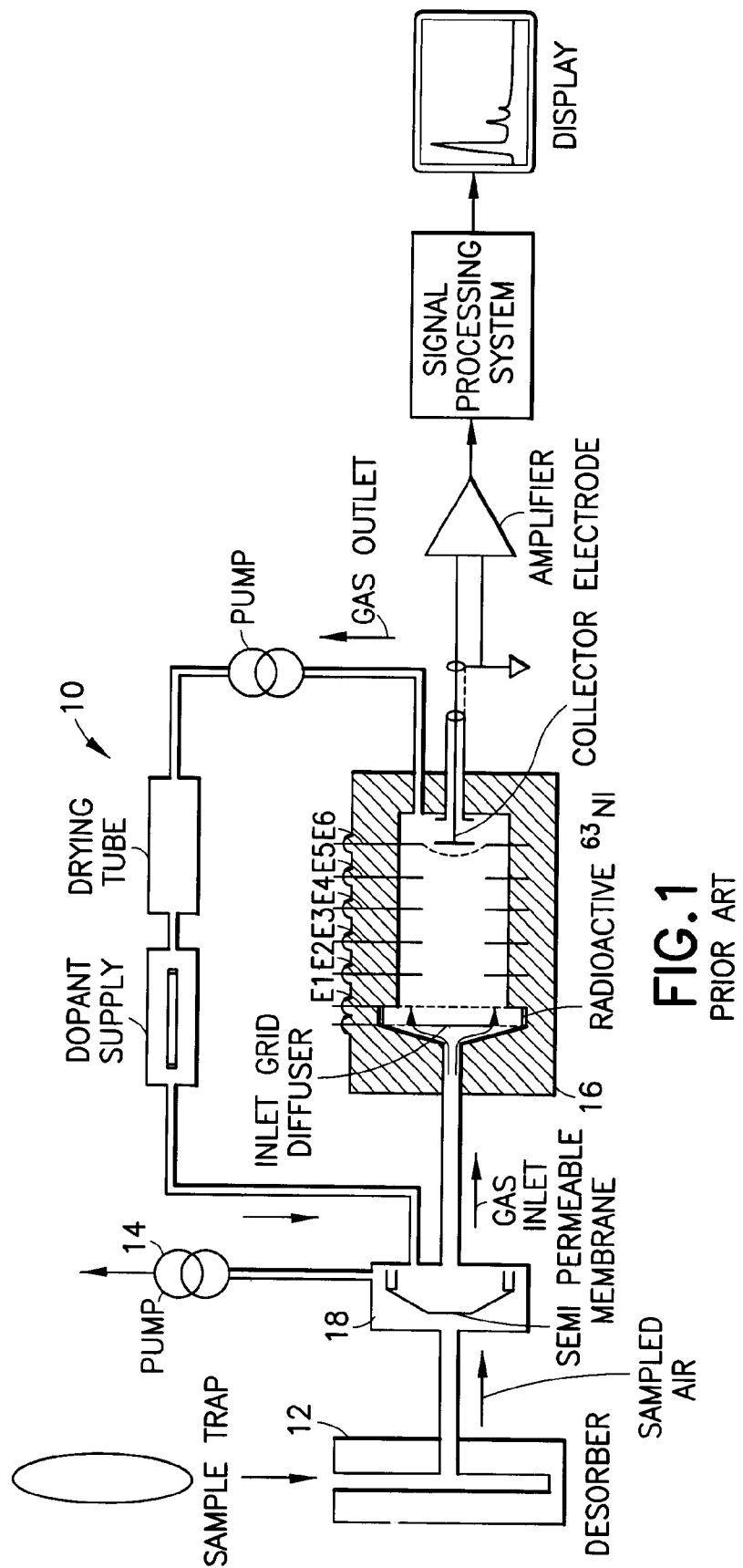
FIG. 1 is a schematic view of a prior art ion trap mobility spectrometer.
Figure 6:
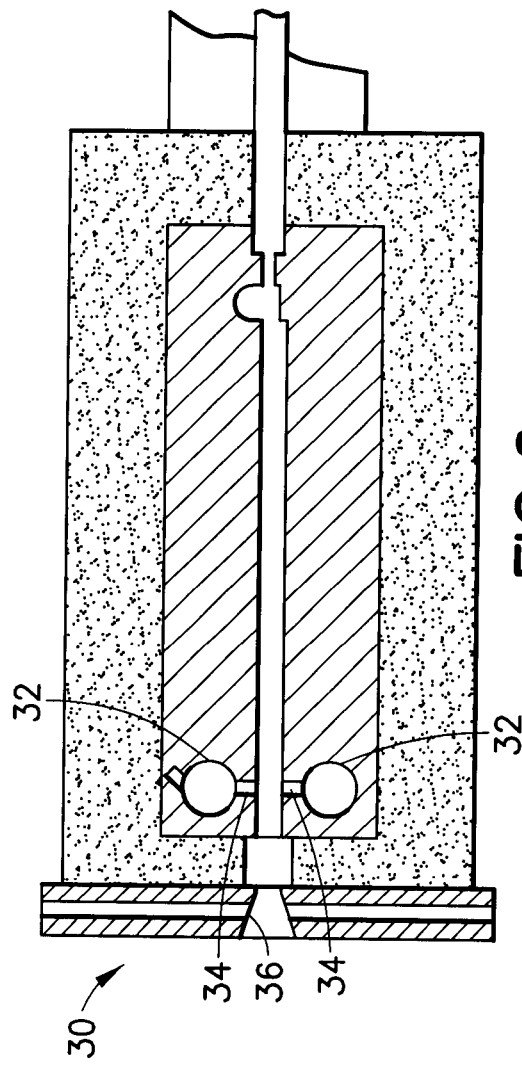
FIG. 6 is a cross-sectional view of a describer for use in a detection system, such as the detection system of FIG. 1.
Figure 7:
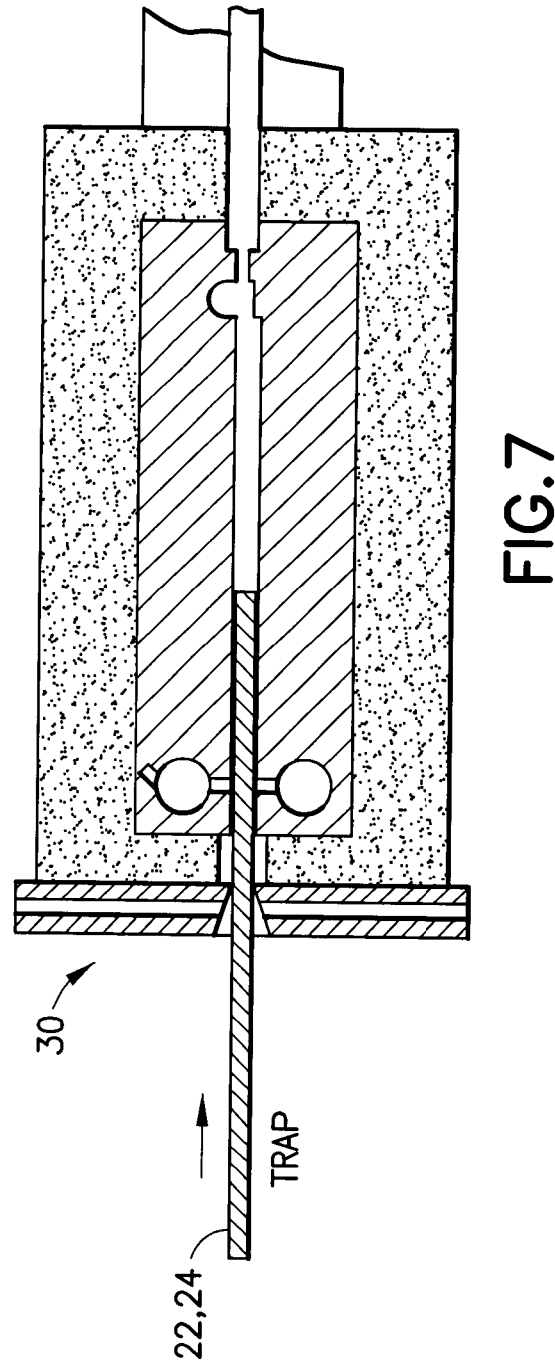
FIG. 7 is a side elevation view similar to FIG. 6, but showing the sample trap being inserted into the desorber.
Figure 8:
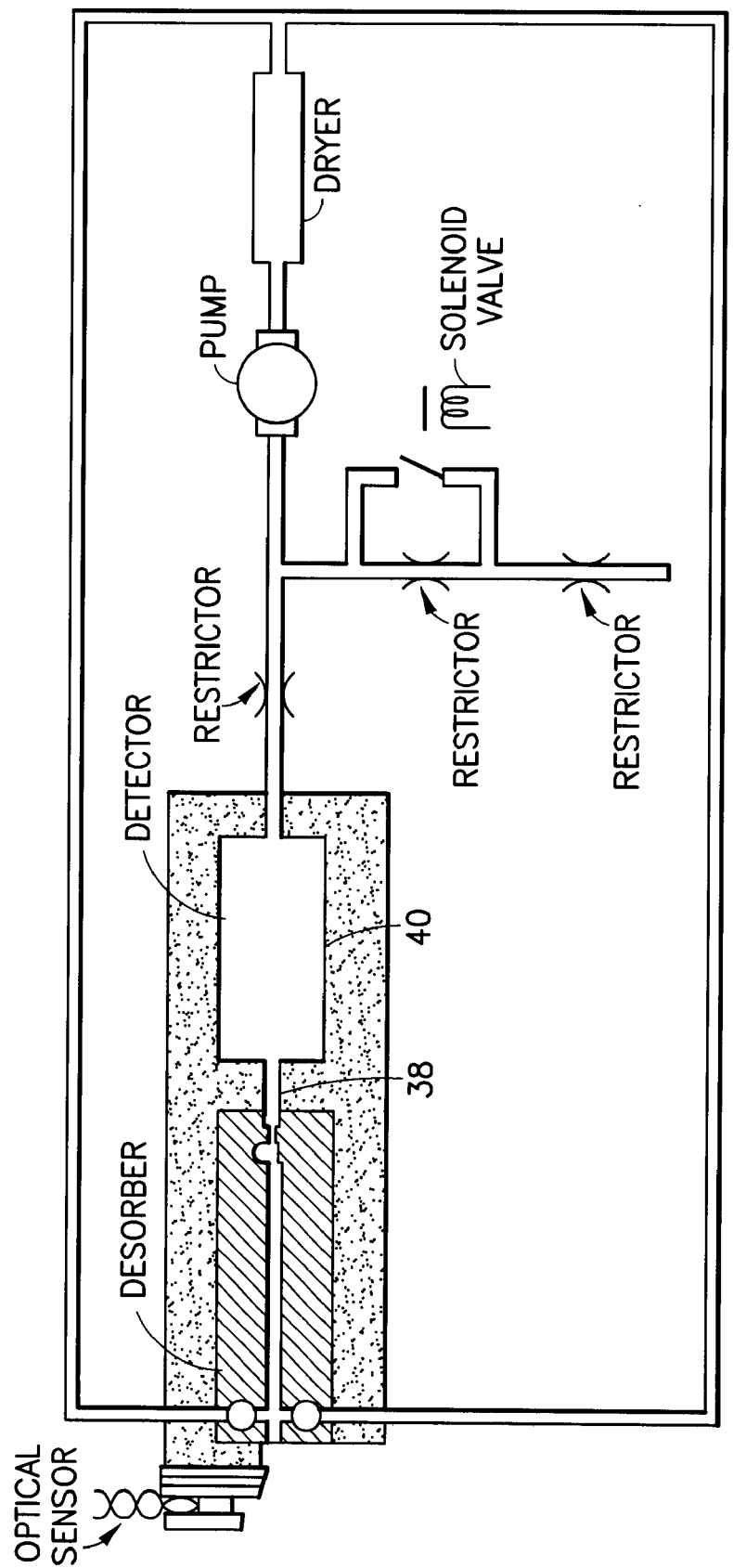
FIG. 8 is a schematic view of the desorber of FIGS. 6 and 7 incorporated into a detection system.

The trap 22 or the trap 24 described and illustrated above may be used in the prior art detection system described above and illustrated in FIG. 1, or in other prior art systems. Alternatively, the sample traps 22 and 24 may be used in a more efficient system that includes a heated desorber as shown, for example, in FIGS. 6 and 7 and as identified generally by the numeral 30. The desorber 30 causes the sample trap 22 or 24 to be purged of unwanted atmospheric constituents, such as water vapor or oxides of nitrogen. More particularly, the sample trap 22 or 24 is pushed into the desorber 30 as shown in FIG. 7. Dry air is fed from the manifold 32 above and below the sample trap through a series of small holes 34 along the mouth 36 of the desorber 30. The dry air passes through the trap 22, 24 and purges out the ambient air in the trap. The purged air passes to the outside atmosphere, thus creating a dry air curtain at the entry to the desorber 30. A portion of the dry air flow fed through the manifold system 32 passes down the desorber 30. As the trap 22, 24 is introduced into the desorber 30, it quickly attains the temperature of the desorber 30. Materials picked up on the trap 22, 24 evaporate and are carried on the stream of dry air into the outlet 38 leading to the detector 40 as shown in FIG. 8. The detector 40 which is illustrated schematically in FIG. 8 may be an ion mobility spectrometer of an ion trap mobility spectrometer as shown in FIG. 1 and as described in greater detail in the above-referenced U.S. Pat. No. 5,491,337.

The trap 22, 24 may be moved relative to the desorber 30 by an automatic actuator. The actuator may push the trap 22, 24 in and out of the desorber 30, but does not entirely eject the trap 22, 24. In the out position of the trap 22, 24, a high flow of air is drawn through the trap 22, 24 by the action of a vacuum pump. Any material which is drawn into the trap is captured and subsequently introduced into the desorber 30 by actuating the trap into the desorber. The material captured by the trap 22, 24 is evaporated in the desorber 30, as described above, and is passed into the detector 40. In this embodiment, the trap system can be incorporated into a walk-through configuration. Here, air may flow over the subject's body, either horizontally or vertically. The air then may be caused to flow through the trap mounted near the test subject, by the action of a suction pump. Vapors and particles entrained in the air sample are trapped in the trap 22, 24 and subsequently are detected as described above and in U.S. Pat. No. 5,491,337.

The apparatus described above with reference to FIGS. 5–8, is particularly useful for the traps 22 and 24 of the subject invention. However, prior art traps also may be employed. Additionally, the walk through the detector described above does not require the trap to be wiped across the surface of the article or subject being tested. Hence, the trap may be formed from a material that could be too abrasive for wiping on a surface. For example, a stainless steel filter material may be used with a walk through trap, including a desorber as described above. The stainless steel filter material provides good trapping efficiency for vapors, as well as good trapping of particles.

Figure 9:
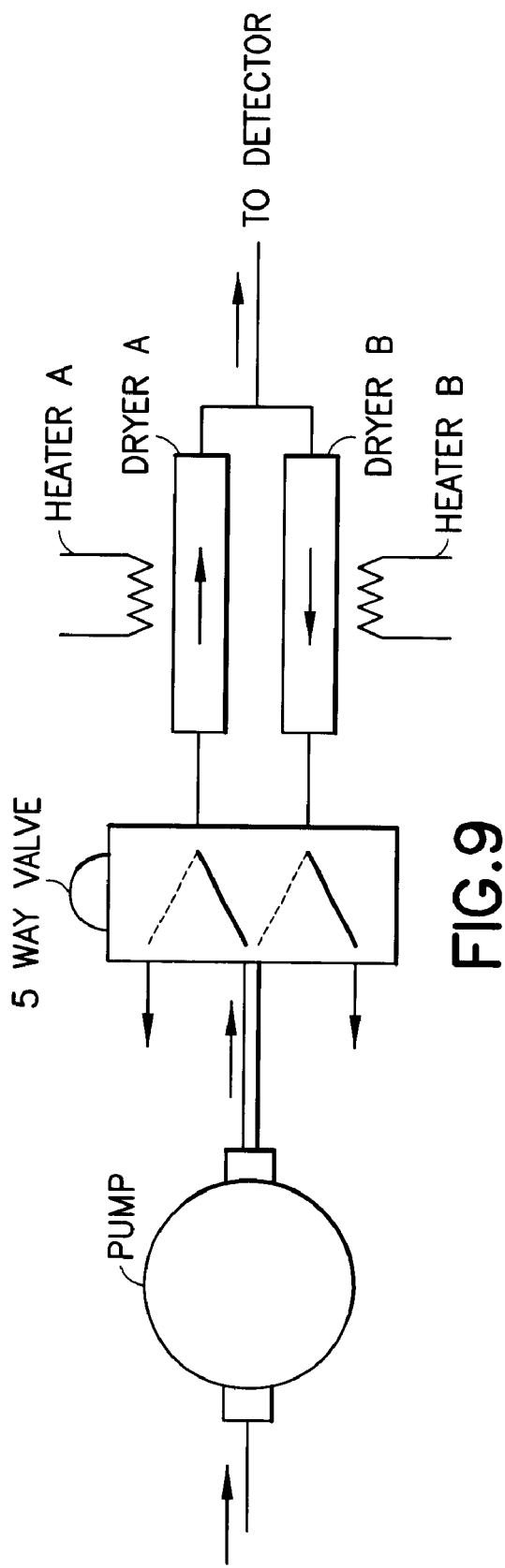
FIG. 9 is a schematic view of a dryer system.

In a further embodiment, the drying material may be recycled automatically by employing two drying tubes as shown in FIG. 9. In the position shown in FIG. 9, a five way valve directs air from the pump through the dryer bed A and to the detector system. Some of this air is directed in the reverse direction through dryer B. At the same time, dryer B is heated by a small heater to a temperature exceeding 100° C. Water is liberated from the dryer and escapes to atmosphere through the five way valve. After a time sufficient to dry most of the water from dryer B, the heater thereof is switched off, and the temperature of dryer B is allowed to fall back to ambient. After a further interval, but before dryer A becomes saturated, the five way valve is switched, thus reversing the flows. Dryer B becomes the active dryer, while dryer A is heated and reactivated. The entire process is either regulated by a timer or by a measure of the humidity of the air being circulated. This cycle may be measured by the detector itself.

What is claimed is:

1. A sample trap for a detection apparatus, said sample trap being formed from an open weave fiberglass fabric coated with a layer of PTFE sufficiently thin to leave open spaces between woven fibers of the fiberglass, the coated fabric being roughened sufficiently to cut through the PTFE at a plurality of locations on said trap.

2. The sample trap of claim 1, wherein the coated fabric is roughened sufficiently to break a plurality of the fibers such that short broken fibers project from the fabric for acting as a scrubbing material to pick up small particles of material to be detected by the detection apparatus.

3. A detector apparatus having a detector for detecting trace amounts of materials of interest carried into the detector through a detector inlet on a stream of air, the detector apparatus comprising flat flexible porous traps formed from a high temperature polyamide fibers, each said trap having a thickness of less than 3 mm, each said trap being for collecting said materials of interest, a desorber having an inlet in the form of a narrow slot dimensioned for receiving one of the traps to be tested for the materials of interest and an outlet communicating with the inlet to the detector, the desorber including a manifold with means substantially adjacent the inlet to the desorber for directing dry air from the manifold and across the inlet to the desorber, a heater for heating the desorber to evaporate materials of interest, in a pump for carrying the materials of interest on the dry air and into the detector, and a dryer assembly for drying air directed into the desorber, the dryer assembly comprising at least first and second dryers and valve means for selectively placing the first and second dryers in communication with the desorber, heaters substantially adjacent the respective dryers and being selectively operable for recharging the dryers.

* * * * *